United States Patent [19]

Parker et al.

[11] Patent Number: 5,247,077
[45] Date of Patent: Sep. 21, 1993

[54] TRI-AZA MACROCYCLES AND PROCESSES FOR THEIR PREPARATION

[75] Inventors: David Parker, Durham; Michael A. W. Eaton, Oxfordshire, both of England

[73] Assignee: Celltech Limited, Berkshire, United Kingdom

[21] Appl. No.: 865,816

[22] Filed: Mar. 31, 1992

Related U.S. Application Data

[63] Continuation of Ser. No. 689,328, Apr. 23, 1991, abandoned.

[51] Int. Cl.$^5$ .............. C07D 255/02; A61K 31/395
[52] U.S. Cl. .................... 540/465; 540/474
[58] Field of Search ................. 540/465, 474

[56] References Cited

U.S. PATENT DOCUMENTS

| | | | |
|---|---|---|---|
| 4,174,319 | 11/1979 | Kobuke | 260/239 |
| 4,174,428 | 11/1979 | Tabushi et al. | 540/474 |
| 4,432,907 | 2/1984 | Wieder et al. | 436/500 |
| 4,472,509 | 9/1984 | Gansow et al. | 436/548 |
| 4,659,839 | 4/1987 | Nicolotti et al. | 548/546 |
| 4,671,958 | 7/1987 | Rodwell et al. | 514/2 |
| 4,678,667 | 7/1987 | Meares | 424/85 |
| 4,877,600 | 10/1989 | Bonnemain et al. | 257/2 |
| 4,885,363 | 12/1989 | Tweedle et al. | 540/465 |
| 5,049,667 | 9/1991 | Schaefer et al. | 540/474 |
| 5,053,503 | 10/1991 | Dean et al. | 540/474 |

FOREIGN PATENT DOCUMENTS

| | | | |
|---|---|---|---|
| 76267/87 | 2/1988 | Australia | 540/465 |
| 0173629 | 8/1985 | European Pat. Off. | 514/184 |
| 0188256 | 7/1986 | European Pat. Off. | 540/465 |
| 0255471 | 7/1987 | European Pat. Off. | 540/465 |
| 0232751 | 8/1987 | European Pat. Off. | 540/474 |
| 88/08422 | 11/1988 | PCT Int'l Appl. | 540/465 |
| 89/01476 | 2/1989 | PCT Int'l Appl. | 540/465 |

OTHER PUBLICATIONS

Broan et al. Chemical Communications (1990) No. 23 pp. 1738–1739.
Chemical Abstracts vol. 114 (1991) Abstract 202872.
Abstracting FEBS Lett. (1991) 280(1) pp. 121–124 (Ramasamy et al.).
Khaw et al., Science. 209, 295 (1980).
Krejcarek et al., Biochem. Biophys. Res. Comm., 77, 581 (1977).

(List continued on next page.)

Primary Examiner—Robert T. Bond
Attorney, Agent, or Firm—Mathews, Woodbridge & Collins

[57] ABSTRACT

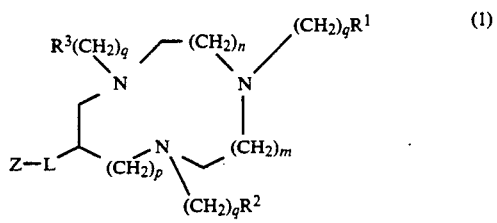

Tri-aza macrocycles of formula (I), wherein m and n, which may be the same or different, is each zero or an integer 1, 2, or 3; p is zero or an integer 1 or 2; q is zero or an integer from 1 to 6 inclusive; $R^1$, $R^2$ and $R^3$, which may be the same or different, is each a hydrogen atom or a group —$CO_2H$ or —$P(O)(XH)R^4$ (where X is an oxygen or sulpher atom and $R^4$ is a hydrogen atom or an alkyl or alkoxy group), with the proviso that at least one of $R^1$, $R^2$ and $R^3$ is a —$P(O)(XH)R^4$ group; L is a covalent bond or a linker group; Z is a hydrogen atom or a reactive functional group; and metal complexes and/or salts thereof; are described together with processes for their preparation and compositions containing them. The compounds are useful as imaging agents, and in the treatment of abnormal cell disorders, such as in the treatment of tumours, and may be coupled to other molecules, such as proteins, for use in diagnosis and therapy.

12 Claims, No Drawings

OTHER PUBLICATIONS

Childs, R. L. and Hnatowich, D. J., J. Nuc. Med. 26, 293 (1985).
Stetter, H., et al., Angew. Chem. Int. Ed. Engl., 15, 686 (1976).
Loncin, J. F., et al., Inorg. Chem., 25, 2646 (1986).
Moi, C. F., et al., J. Am. Chem. Soc., 110, 6266 (1988).
Tweedle, M. F., et al., J. Nuc. Med., 28, 705 (1988).
Goodwin, C. H., et al., J. Nuc. Med., 27, 959 (1986).
Paik, C. H., et al., J. Nuc. Med., 28, 572 (1987).
Paik, C. H., et al., J. Nuc. Med., 29, 889 (1988).
Haseman, C. F., et al., Eur. J. Nuc. Med., 12, 455 (1986).
Parker et al., Pure & Appl. Chem., vol. 61, No. 9, 1637–1641 (1989).
Craig et al., J. Chem. Soc. Chem. Commun. (1989), pp. 794–796.
Cox et al., J. Chem. Soc. Chem. Commun. (1989), pp. 797–798.
Paik et al., J. Nucl. Sci., vol. 30, No. 10, p. 1693–1701 (Oct. 1989).
Paik et al., Nucl. Med. Biol., vol. 16, No. 5, pp. 475–481 (1989).
Deshpande et al., Nucl. Med. Biol., vol. 16, No. 6, pp. 587–597 (1989).
Deshpande et al., The Journal of Nuclear Medicine, "Copper-67-Labeled Monoclonal Antibody Lym-1, A Potential Radio-pharmaceutical for Cancer Therapy: Labeling and Biodistribution in RAJI Tumored Mice", vol. 29, No. 2, pp. 217–225 (Feb. 1988).
Franz, J., et al., Abstract from Journal of Nuclear Medicine, Abstract No. 553, vol. 26, No. 5 (May 1985).
Franz et al., poster exhibited at 32nd Annual Meeting of the Society of Nuclear Medicine prior to May 1985.
Meares, Claude F., Protein Tailoring for Food and Medicine Uses edited by R. E. Feeny et al., "Attaching Metal Ions to Antibodies", pp. 339–352 (1986).
Goodwin, D. A., et al., Abstract of "In Complex of a New Macrocyclic Bifunctional Chelator TETA", presented at European Nuclear Medicine Congress Meeting at Barbican, London, Sep. 3–6 (1985).
Meares et al., Int. J. Cancer Suppl., 2, 99–102 (1988).
Meares et al., Br. J. Cancer, 62, 21–26 (1990).
Gransow et al., ACS Symposium Series, No. 241, "Generator Produced Bi-212" (1984).
Moi et al., Anal. Biochem., 148, 249–253 (1985).

TRI-AZA MACROCYCLES AND PROCESSES FOR THEIR PREPARATION

This is a continuation of application Ser. No. 07/689,328, filed Apr. 23, 1991, now abandoned.

FIELD OF THE INVENTION

This invention relates to functionalised tri-aza macrocycles, to metal complexes thereof, to conjugate compounds containing the functionalised tri-aza macrocycles and metal complexes thereof, and to their use in diagnosis and therapy.

BACKGROUND TO THE INVENTION

The attachment of metal ions to proteins, peptides and other, smaller molecules is a fast expanding technology, which has numerous proven and potential applications in research, in industry and, particularly, in medicine.

In recent years, much of the impetus behind the development of this technology has been the ability to link metal ions to antibodies, especially monoclonal antibodies. Such metal labelled antibodies have found a widespread use, especially in medicine, where they have been employed, for example, to target the metal ions to a specific tissue type, both in vitro and in vivo. Thus, metal labelled antibodies have applications in locating specific tissue types (e.g. employing computer-aided tomographic techniques where the metal ion is in some way detectable) and in the treatment of cell disorders (e.g. treating mammalian tumours where the metal ion is a cytotoxic radionuclide).

Conventionally, attachment of the metal ion to a protein such as an antibody has been achieved by complexation by an acyclic chelate such as a substituted diethylenetriaminepentaacetic acid [Gansow O. A. et al, Inorg. Chem., (1986), 25, 2772, and see for example, U.S. Pat. No. 4454106] or ethylenediaminetetraacetic acid [Meares, C. F. et al, Acc. Chem. Res., (1984), 17, 202] covalently linked to the antibody. Such acyclic complexes however tend to be unstable in vivo either as a result of acid-catalysed decomplexation or competitive chelate binding by $Ca^{2+}$ or $Zn^{2+}$ in serum, or as a result of competition from transferrin [Moerlein, S. M. et al, Int. J. Nuc. Med. Biol., (1981) 8, 277]. The lack of stability can result in uncomplexed metal atoms in the body which have a cytotoxic effect on healthy tissue (e.g. bone marrow) or which markedly reduce the signal-to-noise ratio of an imaging technique.

A possible alternative to the use of acyclic chelates in the labelling of antibodies is the use of macrocyclic ligands, which has previously been suggested in broad terms [Gansow O. A. et al, Am. Chem. Soc. Symp. Ser., (1984), 241, 215; UK Patent Specification No. 2122641; and Moi M. K. et al, Anal. Biochem., (1985), 148, 249–253]. More recently, tri-aza and tetra-aza macrocycles have been described which are capable of binding metals, and which can be conjugated to antibodies (International Patent specifications Nos. WO 89/01475 and WO89/01476).

Other tri-aza macrocycles have also been described, which are capable of binding metals [International Patent Specification No. WO86/02352; European Patent Specification No. 197437; Bryden, C. C. et al, Rare Earths Mod. Sci. Technol. (1982), 3, 53–57; Kabachnik, I. M. et al, Izv. Akad. Nauk. SSSR, Ser. Khim., 835 (1984)]. Some compounds of these types, when complexed with metals, have been proposed for use as contrast agents for use in diagnostic imaging.

We have now found a new class of functionalised tri-aza macrocycles, members of which are able to form kinetically inert complexes with metal ions which are of use in diagnosis and therapy.

SUMMARY OF THE INVENTION

Thus according to one aspect of the present invention we provide a compound of general formula (1):

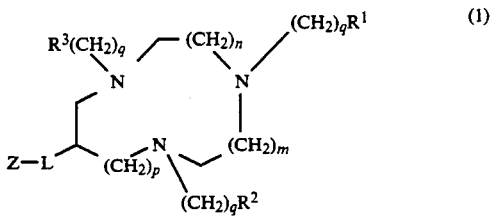

wherein
m and n, which may be the same or different, is each zero or an integer 1, 2, or 3;
p is zero or an integer 1 or 2;
q is zero or an integer from 1 to 6 inclusive;
$R^1$, $R^2$ and $R^3$, which may be the same or different, is each a hydrogen atom or a group —$CO_2H$ or —P(O)(XH)$R^4$ (where X is an oxygen or sulphur atom and $R^4$ is a hydrogen atom or an alkyl or alkoxy group), with the proviso that at least one of $R^1$, $R^2$ and
$R^3$ is a —P(O)(XH)$R^4$ group;
L is a covalent bond or a linker group;
Z is a hydrogen atom or a reactive functional group;
and metal complexes and/or salts thereof.

In the compounds of formula (1), alkyl groups represented by $R^4$ may be for example $C_{1-6}$alkyl groups such as methyl or ethyl groups.

Alkoxy groups represented by $R^4$ may be $C_{1-6}$alkoxy groups such as methoxy or ethoxy groups.

In general, compounds of formula (1) in which $R^1$, $R^2$ and $R^3$ are the same and is each a group —P(O)(XH)$R^4$ are preferred. Compounds of this type in which q is an integer from 1 to 6 inclusive, particularly an integer 1, are especially preferred. Particularly useful compounds of formula (1) are those wherein $R^1$, $R^2$ and $R^3$ is each a group —P(O)(OH)H, —P(O)(OH)OCH$_3$, —P(O)(OH)OCH$_2$CH$_3$ or especially —P(O)(OH)$R^4$ where $R^4$ an alkyl group, particularly a methyl group. In compounds of this type, q is preferably an integer from 1 to 6 inclusive, particularly an integer 1.

In the compounds of formula (1), it will be appreciated that the nature of the group L when it is a linker group may be varied widely without substantially affecting the usefulness of compounds of formula (1) and the metal complexes thereof. Thus L may be any suitable organic radical and may be for example an optionally substituted aliphatic hydrocarbyl chain, optionally interrupted by one or more heteroatoms selected from —O— or —S— or by one or more —N($R^5$)— (where $R^5$ is a hydrogen atom or a $C_{1-6}$alkyl group), —CON($R^5$)—, —N($R^5$)CO—, cycloaliphatic, aromatic, or heteroaromatic groups.

In the above definition, and in the same context whenever it appears below, the term "interrupted by" as applied to cycloaliphatic or aromatic groups is to be understood to also mean that these particular groups may additionally be present linked to the terminal carbon atom of the hydrocarbyl chain represented by L, at the opposite end of the chain to the carbon atom attached to the macrocyle.

Thus, for example, L may be an optionally substituted straight or branched $C_{1-20}$alkylene, $C_{2-20}$alkenylene, or $C_{2-20}$alkynylene chain, optionally interrupted by one or more —O— or —S— atoms or $C_{5-8}$cycloalkylene (e.g. cyclopentylene or cyclohexylene), $C_{6-12}$aromatic (e.g. phenylene or substituted phenylene), $C_{5-10}$heteroaromatic (e.g. furanyl, pyridyl), —N(R$^5$)—, —CON(R$^5$)— or —N(R)$^5$CO— groups.

Examples of substituents which may be present on the chain L include halogen atoms, e.g. fluorine, chlorine, bromine, or iodine atoms or groups selected from $C_{1-6}$alkoxy (e.g. methoxy or ethoxy), hydroxy, nitro, —N(R$^6$)(R$^7$), [where R$^6$ is a hydrogen atom or a $C_{1-6}$alkyl group and R$^7$ is a $C_{1-6}$alkyl group; e.g. —NHCH$_3$ or —N(CH$_3$)$_2$], or substituted amido, e.g. a group of formula —(CH$_2$)$_n$CON(R$^8$)(R$^9$) [where n is zero or an integer 1 to 4 inclusive, R$^8$ is a hydrogen atom or a $C_{1-6}$alkyl group, e.g. methyl and R$^9$ is an optionally substituted $C_{1-6}$alkyl group).

Substituted alkyl groups represented by R$^9$ include for example $C_{1-6}$alkyl groups substituted by one or more halogen atoms, or nitro, amino or hydroxy groups.

In general, in compounds of formula (1) the linker group is preferably an optionally substituted $C_{1-10}$alkylene, (especially $C_{1-6}$alkylene such as methylene, ethylene, propylene butylene, pentylene or hexylene) $C_{2-10}$alkenylene or $C_{2-10}$alkynylene chain optionally interrupted by one or more —O— or —S— atoms or cyclohexylene, phenylene, substituted phenylene, —NH—, —N(CH$_3$)—, —CONH—, —CONH(CH$_3$)— —NHCO— or —N(CH$_3$)CO— groups. Particular examples of linker groups represented by L include, for example, —(CH$_2$)$_d$— (where d is an integer 1 to 4 inclusive),

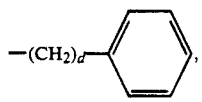

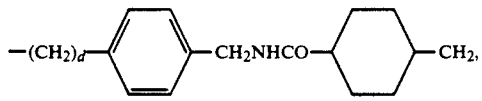

—(CH$_2$)$_d$NHCO(CH$_2$)$_e$— (where e is an integer 1 to 4 inclusive) and —(CH$_2$)$_d$NHCO(CH$_2$)$_e$OCH$_2$—.

The reactive functional group represented by z in compounds of formula (1) may be any group capable of reacting with a thiol, amino, carboxyl, aldehyde, aromatic or heteroaromatic group. Aromatic groups include, for example, phenolic groups. Heteroaromatic groups include for example imidazolyl groups.

Thus, Z may be, for example, a halogen atom, for example a chlorine, bromine or iodine atom or a group selected from —SH, —NH$_2$, hydrazine (—NHNH$_2$) or a derivative thereof, [for example —N(CH$_3$)NH$_2$, —NHCONHNH$_2$, —NHCSNHNH$_2$, or phenyl hydrazine], —NCO, —NCS, —COR$^{10}$, [where R$^{10}$ is a halogen atom such as a chlorine or bromine atom, or a N$_3$, $C_{1-6}$alkoxy, e.g. methoxy, $C_{6-12}$aryloxy (e.g. nitrophenyloxy or dinitrophenyloxy), imidyloxy (e.g. succinimidyloxy) or imidazolyoxy group], imide, e.g. maleimide, a vinyl group of formula —Het$^1$—C(-Het$^2$)=CH$_2$ (where Het$^1$ and Het$^2$, which may be the same or different, is each a nitrogen containing heterocyclic group, e.g. a pyridyl group or Het$^1$ is a nitrogen containing heterocyclic group and Het$^2$ is a hydrogen atom) for example a vinyl pyridyl group of formula

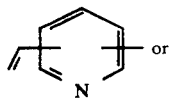 or

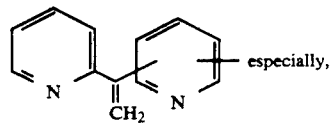 especially,

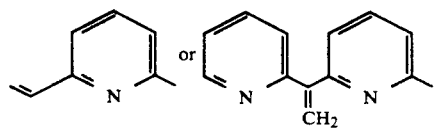 or or a dione of formula

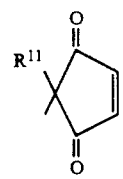

(where R$^{11}$ is a $C_{1-4}$ alkyl e.g. methyl, group).

Metal complexes of the compounds of formula (1) include complexes wheerein the metal is di- or tripositive and has a coordination number from 2 up to 6, especially 6. The metal may be a radioactive isotope. Examples of suitable metals include indium (In), copper(Cu), lead (Pb), bismuth (Bi), cobalt (Co) and gallium (Ga). In, Ga, Co, and Cu are preferred, particularly In and Ga. $^{111}$In, $^{69}$Ga and $^{71}$Ga are particularly preferred.

In general, optimum binding of the metal to the compounds of formula (1) may be achieved by selection of the ring size and where appropriate by adjusting the potential coordination number by choice of the group —(CH$_2$)$_q$R$^1$, —(CH$_2$)$_q$R$^2$, and/or —(CH$_2$)$_q$R$^3$. Thus a particularly important class of compound of formula (1) is that wherein p is zero. Especially useful compounds are those wherein p is zero, m is an integer 1 and n is an integer 1. In general, compounds of formula (1) in which —(CH$_2$)$_q$R$^1$, —(CH$_2$)R$^2$ and —(CH$_2$)$_q$R$^3$ is each —CH$_2$P(O)(OH)R$^4$—where R$^4$ is —H, —OCH$_3$, —OCH$_2$CH$_3$ or an alkyl group, especially a methyl group, are particularly useful.

Salts of the compounds of formula (1) include salts with inorganic or organic bases, for example alkali metal or alkaline earth metal salts such as lithium, sodium, potassium, magnesium or calcium salts; amine salts, such as those from primary, secondary or tertiary amines, for example ethanolamine, diethanolamine, morpholine, glucamine, N-methylglucamine or N-N-dimethylglucamine salts; and amino acid salts such as lysine, arginine and ornithine salts; or acid addition salts such as hydrobromides or hydrochlorides. Pharmaceutically acceptable salts are particularly preferred.

An important group of compounds according to the invention has the formulae (1a):

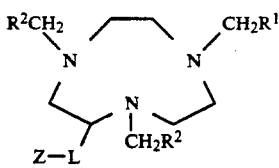

(1a)

wherein $R^1$, $R^2$, $R^3$, L and Z are as defined for formula (1) and metal complexes and/or salts thereof.

Compounds of this type in which $R^1$, $R^2$, and $R^3$ is each $P(O)(OH)R^4$ where $R^4$ is —H, —OCH$_2$CH$_3$ or, especially —CH$_3$ are particularly preferred.

Compounds of formula (1a) in which L is a linker group [particularly those specifically identified for compounds of formula (1)] are especially useful. Particular groups of this type are those of formulae —(CH$_2$)$_d$— and —(DH$_2$)$_d$NHCO(CH$_2$)$_e$—, where d and e, which may be the same or different is each an integer 1 to 4 inclusive.

Z in compounds of formula (1a) is preferably a reactive functional group, [particularly those specifically identified for compounds of formula (1)], especially a group of formula —NH$_2$, —COR$^{10}$, —Het$^1$—C(-Het$^2$)=CH$_2$ or a dione of formula:

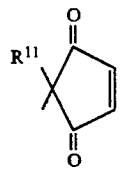

Indium and gallium complexes of the compounds of formula (1a) are particularly useful.

A further group of compounds of formula (1a) which is particularly useful is that wherein L in the compounds is a covalent bond, and Z is a hydrogen atom, and metal complexes and/or salts thereof. Gallium complexes of compounds of this type are particularly important, especially $^{71}$Ga complexes, and particularly gallium complexes where $R^1$, $R^2$, and $R^3$ is each $P(O)(OH)R^4$, especially $P(O)(OH)CH_3$.

The compounds of formula (1) and the metal complexes and/or salts thereof have a diagnostic use, for example as imaging agents in vitro and in vivo. The compounds of formula (1a) and the salts thereof are especially useful for use as imaging agents, particularly the gallium complexes, which are particularly useful in nuclear magnetic reasonance imaging, especially the gallium (particularly $^{71}$Ga) complexes of formula (1a) wherein L is a covalent bond, Z is a hydrogen atom and $R^1$, $R^2$ and $R^3$ is each a group $P(O)(OH)R^4$ especially $P(O)(OH)CH_3$ and the salts thereof The compounds of formula (1) and the metal complexes and/or salts thereof are also cytotoxic agents and may be used in the treatment of abnormal cell disorders, for example in the treatment of tumours. For use as diagnostic and/or therapeutic agents, the compounds may be employed using conventional methods (e.g. for formulation and presentation), already is use for metal complexing reagents.

For application of the compounds of formula (1) as imaging or cytotoxic agents, it may be preferable to couple the compounds to other molecules such as proteins, especially antibodies, peptides or carbohydrates to form conjugate compounds, and the compounds of formula (1) are particularly well adapted for use in this respect.

The compound of formula (1) may be coupled through any thiol, amino, carboxyl, hydroxyl, aldehyde, aromatic or heteroaromatic group present in the protein, peptide or carbohydrate.

Thus in a further aspect of the invention, we provide a conjugate compound which comprises a compound of formula (1) or a metal complex and/or salt thereof, coupled to a protein, peptide or carbohydrate.

It is to be understood that a conjugate compound according to the invention may comprise more than one molecule of a compound of formula (1) coupled to any one protein, peptide or carbohydrate molecule.

In a particular aspect, the invention provides a conjugate compound of formula (2):

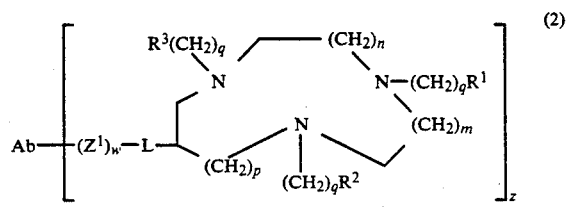

(2)

wherein m, n, p, q, $R^1$, $R^2$, $R^3$, and L are as defined for formula (1);

$Z^1$ is the residue of a reactive functional group;

w is zero or an integer 1;

z is an integer 1 or more;

Ab is an antibody; and metal complexes and/or salts thereof.

In the compound of formula (2), the residue or a reactive functional group represented by $Z^1$ may in general be the residue of a reactive functional group Z as defined for formula (1).

In particular, $Z^1$ may be for example —S—, —NH— —NHN=, —N(CH$_3$)N=, —NHCONHN=, —NHCSNHN=, —N(Ph)N= (where Ph is phenyl), —NC(O)—,

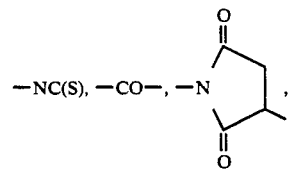

—NC(S), —CO—, —N

—Het$^1$—C(Het$^2$)CH$_2$— or

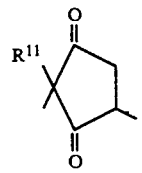

The antibody in the conjugates of formula (2) may in general belong to any immunoglobulin class. Thus for example it may be an immunoglobulin M antibody or, in particular, an immunoglobulin G antibody. The antibody molecule may be of animal, for example mammalian origin, and may be for example of murine, rat or human origin. It may be a natural antibody or a fragment thereof, or, if desired, a recombinant antibody or antibody fragment i.e. an antibody molecule or antibody fragment which has been produced using recombinant DNA techniques.

Particular recombinant antibodies or antibody fragments include, (1) those having an antigen binding site at least part of which is derived from a different antibody, for example those in which the hypervariable or complementarity determining regions of one antibody have been grafted into the variable framework regions of a second, different antibody (as described in European Patent Specification No. 239400); (2) recombinant antibodies or fragments wherein non-Fv sequences have been substituted by non-Fv sequences from other, different antibodies (as described in European Patent Specification Nos. 171496, 173494 and 194276; or (3) recombinant antibodies or fragments possessing substantially the structure of a natural immunoglobulin but wherein the hinge region has a different number of cysteine residues from that found in the natural immunoglobulin, or wherein one or more cysteine residues in a surface pocket of the recombinant antibody or fragment is in the place of another amino acid residue present in the natural immunoglobulin (as described in International Patent Applications Nos. PCT/GB 88/00730 and PCT/GB 88/00729 respectively).

The antibody may be of polyclonal or, preferably, monoclonal origin. It may be specific for any number of antigenic determinants, but is preferably specific for one. The antigenic determinants may be any hapten or antigenic determinant associated with any antigen. Particular antigens include those associated with animals, e.g. humans, [for example normal animal tissue or organ cell-associated antigens, tumour cell-associated antigens (for example oncofetal antigens such as carcinoembryonic antigen or alphafetoprotein, placental antigens such as chorionic gonadotropin and placental alkaline phsophatase, and prostate antigens such as prostatic acid phsophatase and prostate specific antigen) and antigens associated with components of body fluids such as fibrin or platelets], viruses, bacteria and fungi.

In a preferred aspect the antibody may be capable of recognising and binding a tumour cell-associated antigen, particularly one or more epitopes on the TAG-72 antigen associated with human breast and colon tumours. A particularly preferred antibody of this type is the monoclonal antibody B72.3 [Colcher, D. et al Proc. Nat. Acad. Sci. USA (1981), 78 3199] or a fragment thereof, particularly a F(ab')2 fragment.

The antibody Ab will in general be coupled to the remainder of the conjugate of formula (2) (i.e. the macrocycle and linker) through any appropriate reactive atom or group, for example a nitrogen or, especially, sulphur atom, present in the antibody. It will be appreciated that any one antibody molecule may contain more than one reactive group capable of coupling with the macrocycle and linker. Thus, for example, z in the conjugates of formula (2) may be an integer 1, 2, 3, 4, 5, 6 or more depending on the number of macrocycles linked to any particular antibody molecule or fragment.

Indium and gallium complexes of conjugates of formula (2) are particularly useful.

It is to be understood that the definitions and preferences expressed for m, n, p, q, $R^1$, $R^2$, $R^3$ and L in compounds of formula (1), and for classes of compounds of formula (1) are also applicable to conjugates of formula (2).

Particularly useful conjugate compounds according to the invention are those comprising a compound of formula (1a), or a metal complex and/or salt thereof, coupled to an antibody. The indium and gallium complexes of these conjugates are especially important.

The compounds of formulae (1) and (2) may be formulated for use in accordance with conventional practice, and thus according to a further respect of the invention we provide a composition comprising a compound of formula (1) or a compound of formula (2) or a metal complex and/or salt thereof, together with one or more pharmaceutically acceptable carriers.

Particularly suitable compositions according to the invention are those adapted for parenteral administration, especially intravenous administration. Suitable formulations of this type include solutions of the compounds of formulae (1) or (2) in isotonic saline.

The quantities of compounds of formulae (1) or (2) used in formulations according to the invention will vary according to the intended use (i.e. imaging or therapy) and other variables such as the intended cell target, but may be easily determined in accordance with conventional practice for reagents of this type.

Compounds of the invention may be prepared by the following processes wherein the groups and symbols $R^1$, $R^2$, $R^3$, m, n, p, q, L, Z, Ab and z are as defined for formulae (1) and (2) except where stated otherwise. Where a metal complex is desired as a final product, the complexation with a metal atom may be carried out as a final step in the production process, as described below for the complexation of compounds of formula (1), or alternatively it may be desirable to complex the metal at an earlier stage in the process, providing of course that the requisite macrocycle structure is present. In the following processes, it may be desirable to use starting materials in which the group Z is in a protected state, or which contain a precursor of the group, as discussed below.

Thus, according to a further aspect of the invention a compound of formula (1) [wherein q is an integer 1–6 and, where present, in $R^1$, $R^2$ and/or $R^3$ the group X is an oxygen atom] or a metal complex thereof may be prepared by reaction of a corresponding compound of formula (3)

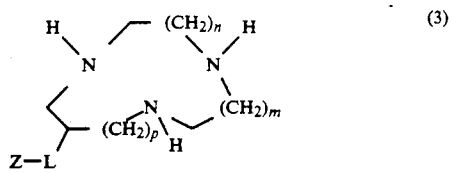

or a metal complex thereof, with a reagent
$D(CH_2)_qP(O)(OR^{13})R^4$, or $D(CH_2)_qP(O)(OR^{13})_2$,
(where D is a displaceable group, for example a halogen atom such as a bromine atom; $R^{13}$ is a $C_{1-4}$alkyl, e.g. methyl or ethyl group; and q and $R^4$ are as defined previously) followed where necessary by hydrolysis.

The reaction may be performed in a solvent such as water or an organic solvent such as a nitrile e.g. acetonitrile or an alcohol, e.g. ethanol or an amide e.g. dimethylformamide in the presence of a base such as an alkali metal carbonate or hydroxide, e.g. sodium, potassium or caesium carbonate, or sodium, potassium or lithium hydroxide, at an elevated temperature e.g. the reflux temperature.

Where appropriate, hydrolysis may be achieved using a base, such as described above, in a suitable solvent, for example sodium hydroxide in an alcohol such as ethanol.

In this reaction, the group Z may need to be in a protected state. Conventional protecting groups may be used, depending on the nature of Z, and may be removed using standard procedures, once the desired reaction has been effected.

Reagents $D(CH_2)_qP(O)(OR^{13})R^4$ and $D(CH_2)_qP(O)(OR^{13})_2$ may be prepared by heating compounds of formulae $P(OR^{13})_2R^4$ or $P(OR^{13})_3$ with a compound $(CH_2)_qD_2$.

In an alternative process, a compound of formula (1) [wherein in $R^1$, $R^2$ and/or $R^3$ the group X where present is an oxygen atom] may be prepared by reaction of a compound of formula (3), or a metal complex thereof with a phosphine $R^4P(OR^{13})$ in the presence of suitable aldehyde (for example formaldehyde or paraformaldehyde), followed by hydrolysis.

The reaction may be performed in an organic solvent, e.g. a nitrile, alcohol, or amide, or an ether such as tetrahydrofuran at an elevated temperature, for example the reflux temperature. Hydrolysis may be achieved using an acid, for example an inorganic acid such as hydrochloric acid, at an elevated temperature such as the reflux temperature.

Compounds of formula (1) may also be prepared by interconversion from other compounds of formula (1). Thus one functional group Z may be exchanged for another and, if desired a linker group L changed to another by appropriate manipulative reactions. For example, a compound of formula (1) where —L—Z is a group —$L^1$—NHCO—$L^2$—Z (where —$L^1$—NHCO—$L^2$ represents the group L) may be prepared by reaction of a corresponding compound wherein —L—Z represents —$L^1$—$NH_2$ with a reagent $R^bO$—$L^2$—Z (where $R^b$ is for example an imide, such as succinimide, or a substituted phenyl group such as a p-nitrophenyl group) in the presence of a tertiary amine, such as diisopropylethylamine, is a solvent such as dimethylformamide.

Reagents of formula $R^bO$—$L^2$—Z are either known or may be obtained from known starting materials using methods analogous to those used for the preparation of the known compounds.

In another interconversion process, a compound of formula (1) wherein X where present is a sulphur atom may be prepared by reaction of a corresponding compound wherein X is an oxygen atom by reaction with a sulphide, for example phosphorous pentasulphide, at an elevated temperature.

It will be appreciated that where it is desired to prepare a compound of formula (1) in which one or two of $R^1$, $R^2$ and $R^3$ are a hydrogen atom or a $CO_2H$ group this may be achieved by first selectively N-protecting the compound of formula (3) or a precursor using an appropriate amine protecting group(s), for example a p-toluenesulphonyl group in accordance with conventional practice. Reaction of the N-protected compound (3) to introduce the required group —P(O)(XH)$R^4$ using the methods described above followed by deprotection and further reaction with a group $D(CH_2)_qH$ or $D(CH_2)_qCO_2H$ (or an acid protected form thereof) using the reagents and conditions described previously for the introduction of the group —P(O)(XH)$R^4$ then yields the desired compound in which one or two of $R^1$, $R^2$ and $R^3$ are —H or $CO_2H$.

Where metal complexes of compounds of formulae (1) or (2) are required (or any other suitable macrocyclic intermediate described herein) these may be prepared by treating the compound with a metal salt (for example a metal halide e.g. a chloride, or a nitrate, acetate, carbonate or sulphate) or a metal oxide in an appropriate solvent for example an aqueous or non aqueous solvent, (e.g. acetonitrile, acetone, propylene carbonate, dimethylformamide or dimethylsulphoxide) at any suitable temperature from 0° C. to 100° C. such as 10° C. to 80° C. e.g. around 60° C.

A conjugate compound of formula (2) or a metal complex thereof may be prepared by reaction of a corresponding compound of formula (1) or a metal complex thereof with an antibody Ab (as previously defined).

The reaction may be performed in a suitable solvent, for example an aqueous solvent such as a phosphate buffer, at an appropriate temperature, for example at 0° C.-30° C., especially 0°-10° C. e.g. 4° C.

The antibody Ab may be obtained using procedures well known in the art. If desired, before the coupling reaction, the antibody may first be treated to yield appropriate groups for reaction with the compound of formula (1). Thus for example the antibody may be subjected to oxidation, for example periodate oxidation to yield aldehyde groups, or, in particular, may be treated with a reagent [e.g. Traut's reagent (2-iminothiolane)] using standard procedures to generate free sulphydryl groups in the molecule.

Salts of compounds of formulae (1) or (2) and their metal complexes may be prepared by conventional means, for example by reaction of a compound of formulae (1) or (2) with an appropriate base or acid in a suitable aqueous or non-aqueous solvent as described above, at any suitable temperature from 0° C. to 100° C.

Intermediates of formula (3) may be prepared by the methods described in International Patent Specification Publication No. WO 89/01475.

The invention is illustrated by the following Examples:

EXAMPLE 1

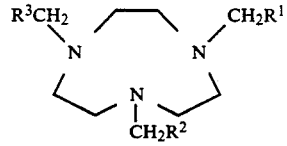

(a) $R^1$, $R^2$, $R^3$ is each $P(O)(OCH_2CH_3)CH_3$
(b) $R^1$m $R^2$, $R^3$ is each $P(O)(OH)CH_3$
(c) Indium complex of (b)
(d) Gallium complex of (b)

(a) To a solution of 1,4,7-triazacyclononane (90 mg) and paraformaldehyde (0.10 g) in dry tetrahydrofuran (5 ml) was added methyl diethoxyphosphine (0.5 g) and the solution was boiled under reflux (under $N_2$) for 48 h. After removal of solvent, the residue was chromatographed on neutral alumina (eluant 0→5% methanol/$CH_2Cl_2$) to yield the desired triester product as a pale-yellow oil, Rf=0.51 (3% methanol—$CH_2Cl_2$). ∂p ($CD_2Cl_2$) 54.2. m/e (DCI, $CH_2Cl_2$) 491, 490 [M+ +1]382, 289.

(b) The triester from (a)(50 mg) was treated with hydrochloric acid (6M, 2 ml) and was heated to 110° for 18 h. Removal of solvent yielded the desired triacid as a glassy solid m/e (FAB, m-nitrobenzylalcohol) 406 (M++1). ∂p (H₂O, pH 1) 42.5. δ$_H$ (D₂O) 3.32 (18H, mult., CH₂CH₂N,+CH₂P), 1.42 (9H, d, J=14, P—CH₃).

Admixture of equimolar quantities of the triacid prepared in (b) and either a solution of indium nitrate in dilute nitric acid (pH 1) or gallium nitrate in nitric acid (pH 1) yielded solutions of the corresponding complexes quantitatively with the following characteristics:

(c) Indium complex: ∂p (H₂O, pH 1)+38.3-invariant over 4 weeks at pH 1

(d) Gallium complex: ∂p (H₂O, pH 1)+40.5; ∂ Ga(H₂O, pH 1) +137 ppm (invariant pH 0 for 1 week); m/e (DCI methanol)=474, 472 (M++1).

EXAMPLE 2

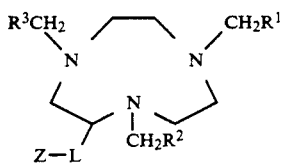

(a) R¹, R², R³ is each P(O)(OCH₂CH₃)CH₃; L—Z is —(CH₂)₄NHCO-phenyl (b) R¹, R², R³ is each P(O)(OH)CH₃; L—Z is —(CH₂)₄NH₂.

(c) R¹, R², R³ is each P(O)(OH)CH₃; L—Z is —(CH₂)₄NHCO(CH₂)₂CO₂—Ph where Ph is 4-nitrophenyl.

(a) To a solution of 2-(4-N-benzamidyl)butyl-1,4,7-triazacyclononane [prepared as described in International Patent Specification No. WO 89/01475] (0.39 g) in dry tetrahydrofuran (10 ml) was added methyldiethoxyphosphine (0.66 g) and paraformaldehyde (0.18 g) and the mixture was heated to reflux for 18h with removal of water (Soxhlet: 4A molecular sieves). After filtration and removal of solvent, the residue was purified by chromatography on neutral alumina (0→3% methanol in CH₂Cl₂) to yield the desired tri-ester product as a colourless oil (0.26 g). m/e (d.c.i.) 665 (M++1), 557, 437, 126, 109, δ$_C$(CDCl₃) 167.4 (carbonyl); 134.75, 130.67, 121.86, 127.10 (aryl); 63.48 (CH₂O); 59.87, 59.03, 58.2, 58.15, 57.9, 57.8, 57.0, 53.1, 53.0, 52.7, (CH₂N); 39.4, 39.35 (CH₂NHCO, diastereoisomers); 28.6 (br.s, CH₂C); 24.0, 23.9 (CH₂C); 16.40, 16.36 (CH₃CH₂O: diastereomers); 13.22 (d, J$_{CP}$89 Hz, major), 12.95, 12.80 (d+d, J$_{CP}$=90, 91 Hz, CH₃P minor diastereoisomers) ν max (film) 3405, 3200 (NH); 2960, 2915, 2825 (CH); 1640 (NHCO,s); 1205 (vs); 1035 (vs), 950 (s) cm⁻¹. δ$_H$ (CDCl₃) 7.91 (2H, dd, ortho arom.), 7.85 (1H, br. t, NHCO), 7.45-7.39 (3H, para+meta arom CH), 4.02 (6H, mult, CH₂O), 3.50-2.60 (19H, mult, CHN+CH₂N) 1.63 (2H, mult, CH₂CH₂NHCO) 1.55-1.42 (4H, mult, CH₂C), 1.30 (9H, mult, CH₃P), 1.20 (9H, t+t+t, CH₃CH₂O, diastereomers)

(b) A solution of the triester (0.13 g), prepared in (a) in hydrochloric acid (6M, 5 ml) was heated to reflux for 24 h. After cooling, washing with ether (3×2 ml), dichloromethane (2×5 ml) and evaporation under high vacuum (0.01 mm Hg, 18 h), a colourless glass was obtained of the tetrahydrochloride salt of the corresponding triacid in which L—Z is (CH₂)₄NH₂. m/e (F.a.b.; glycerol): 477 (M+).

(c) To solution of the triacid prepared in (a) (0.048 g) in dry DMSO (0.5 ml) was added N-methylmorpholine (90 mg) and di-(p-nitrophenyl)-succinate (54 mg) and the mixture was stirred for 18 h at 20° C., monitoring by HPLC (Dynamax C18 60A, 21.4 mm column: A=0.1% trifluoroacetic acid —H₂O), C=0.1% trifluoroacetic acid —CH₃CN: t=0 A=95%, C=5%; t=20 min A=5%, C=95%; flow=10 ml min⁻¹) R$_t$=12 mm. Purification by HPLC afforded the desired tri-acid as a colourless solid (25 mg). m/e (F.a.b., glycerol) 699 (M+). δ$_H$(D₂O) 8.30 (2H, ortho Ar), 7.34 (2H, ortho Ar), 4.0 2.5 (23H, mult, CH₂CO+CH₂N), 1.8-1.5 (6H, mult, CH₂C), 1.25 (d+d+d, 9H, CH₃P).

Reaction of the compound of part (c) with gallium nitrate or indium nitrate as described in Example 1 yielded the corresponding gallium or indium complexes.

We claim:

1. A compound of the formula:

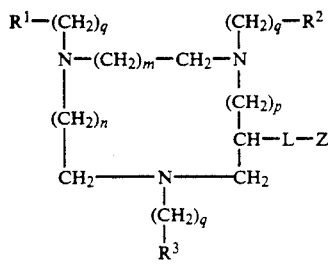

wherein:
each of m and n, independently of the other, has a value of from 0 to 3;
p has a value of from 0 to 2;
q has a value of from 0 to 6;
at least one of R¹, R², and R³ is —P(O)(XH̄)R⁴ and the other two of R¹, R², and R³, independently of the other, is hydrogen, —COOH, or —P-(O)(XH)R⁴;
in which
X is oxygen or sulfur, and
R⁴ is hydrogen, alkyl of 1 to 6 carbon atoms, or alkoxy of 1 to 6 carbon atoms;
Z is selected from the group consisting of halo, hydroxy, thiol, amino, hydrazino, —N=C=O, —N=C=S, —COR¹⁰, imido, vinylpyridinyl, pyridinyl, and 2-R¹¹-cyclopent-4-ene-1,3-dione,
in which
R¹⁰ is halo, azido, alkoxy of 1 to 6 carbon atoms, aryloxy of 6 to 12 carbon atoms, imidyloxy, or imidazoyloxy and
R¹¹ is alkyl of 1 to 4 carbon atoms; and
L is an alkylene chain of from 1 to 20 carbon atoms, an alkenylene chain of from 2 to 20 carbon atoms, or an alkynylene chain of from 2 to 20 carbon atoms which chain is uninterrupted or interrupted with a —O—, —S—, —N(R⁵)—, —CON(R⁵)—, or —N(R⁵)CO— group in which R⁵ is hydrogen or alkyl of 1 to 6 carbon atoms, or with a divalent cycloaliphatic ring of 5 to 8 carbon atoms, a divalent benzene ring, or a divalent pyridine ring which is unsubstituted or substituted as hereinafter set forth, said L being unsubsituted or substituted with one or more members selected from the group consisting of halo, alkoxy of 1 to 6 carbon atoms, hydroxy, nitro, —N(R⁶R⁷), and —(CH2)-$_n$CON(R⁸R⁹) in which
R⁶ is hydrogen or alkyl of 1 to 6 carbon atoms, $R^7$ is alkyl of 1 to 6 carbon atoms,
$R^8$ is hydrogen or alkyl of 1 to 6 carbon atoms,
$R^9$ is alkyl of 1 to 6 carbon atoms, unsubstituted or substituted with halo, nitro, amino, or hydroxy, and
n has a value of from 0 to 4.

2. A compound according to claim 1 having the formula:

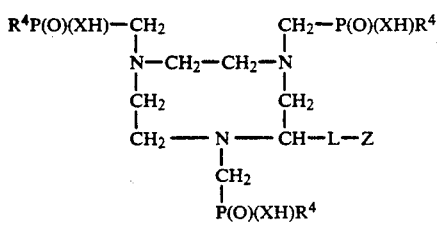

wherein each of X, $R^4$, Z, and L is as therein defined.

3. A compound according to claim 2 wherein $R^4$ is methyl and X is oxygen.

4. A compound according to claim 1 wherein Z is amino, 6-vinylpyridin-1-yl, 6-[1-(1-pyridyl)eth-1-en-1-yl]pyridin-1-yl, or 2-$R^{10}$-cyclopent-4-ene-1,3-dione.

5. A compound according to claim 1 wherein —L— is —(CH$_2$)$_d$— or —(CH$_2$)$_d$—NHCO—(CH$_2$)$_e$— wherein each of $d$ and $e$, independently of the other, has a value of from 1 to 4.

6. A compound according to claim 1 having the formula:

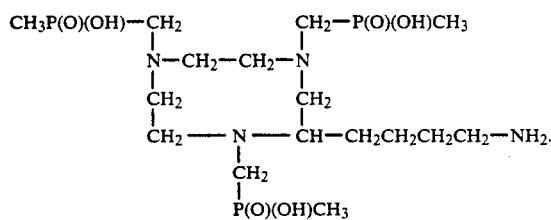

7. A compound according to claim 1 having the formula:

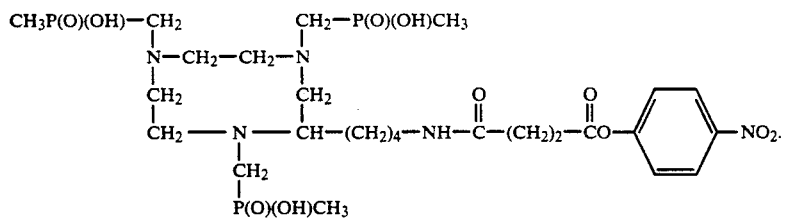

8. A compound of the formula:

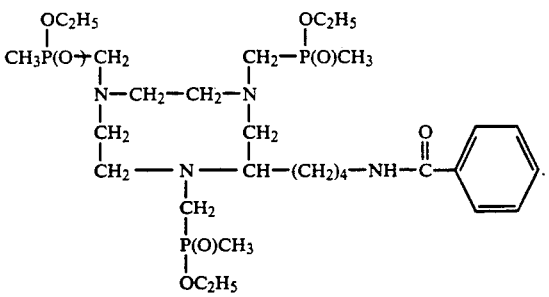

9. A complex of a compound according to claim 1 with indium, copper, lead, bismuth, cobalt, or gallium.

10. A complex according to claim 9 wherein the metal is indium or gallium.

11. A compound of the formula:

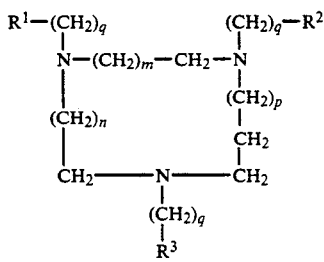

wherein:
each of m and n, independently of the other, has a value of from 0 to 3;
p has a value of from 0 to 2;
q has a value of from 0 to 6; and
at least one of $R^1$, $R^2$, and $R^3$ is —P(O)(XH)$R^4$ and the other two of $R^1$, $R^2$, and $R^3$, independently of the other, is hydrogen, —COOH, or —P(O)(XH)$R^4$;
in which
X is oxygen or sulfur, and
$R^4$ is hydrogen, alkyl of 1 to 6 carbon atoms, or alkoxy or 1 to 6 carbon atoms.

12. A complex of a compound according to claim 11 with gallium.

* * * * *

UNITED STATES PATENT AND TRADEMARK OFFICE
CERTIFICATE OF CORRECTION

PATENT NO. : 5,247,077
DATED : September 21, 1993
INVENTOR(S) : David Parker, et. al.

It is certified that error appears in the above-indentified patent and that said Letters Patent is hereby corrected as shown below:

Column 12, Claim 1, line 47, change "pyridinyl" to --[1-(pyridyle)ethen-1-yl]pyridinyl--.

Signed and Sealed this

Seventh Day of June, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO : 5,247,077

DATED : September 21, 1993

INVENTOR(S) : David Parker, et. a l.

It is certified that error appears in the above-identified patent and that said Letters Patent is hereby corrected as shown below:

Column 12, Claim 1, line 47, should read -- "[1-(pyridyl) ethen-1-yl]pyridinyl"--.

This certificate supersedes Certificate of Correction issued June 7, 1994.

Signed and Sealed this

Twenty-ninth Day of November, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO : 5,247,077
DATED : September 21, 1993
INVENTOR(S) : David Parker, et. al.

It is certified that error appears in the above-identified patent and that said Letters Patent is hereby corrected as shown below:

Column 12, Claim 1, line 47, change "pyridinyl" to -- [ 1- (pyridyl) ethen-1-yl] pyridinyl --.

This certificate supersedes Certificate of Correction issued November 29, 1994.

Signed and Sealed this

Thirty-first Day of January, 1995

*Attest:*

BRUCE LEHMAN

*Attesting Officer*    *Commissioner of Patents and Trademarks*